United States Patent [19]

Ross

[11] Patent Number: 5,196,565
[45] Date of Patent: Mar. 23, 1993

[54] EXTRACTIVE PURIFICATION OF PHENOLS

[75] Inventor: John R. Ross, Mobile, Ala.

[73] Assignee: Ciba-Geigy Corporation, Ardsley, N.Y.

[21] Appl. No.: 904,806

[22] Filed: Jun. 26, 1992

[51] Int. Cl.$^5$ ............... B29B 9/10; C07C 69/78; C07C 69/88
[52] U.S. Cl. ...................... 560/55; 560/67; 264/9
[58] Field of Search ............ 560/61, 55, 67; 264/9

[56] References Cited

U.S. PATENT DOCUMENTS

| | | | |
|---|---|---|---|
| 4,242,224 | 12/1980 | Dean, II et al. | 524/255 |
| 4,316,996 | 2/1982 | Collonge et al. | 568/785 |
| 4,386,224 | 5/1983 | Deefman | 568/780 |
| 4,668,725 | 5/1987 | Broussard et al. | 560/61 |
| 4,694,099 | 11/1987 | Ahlfors et al. | 560/61 |
| 5,006,284 | 4/1991 | Gahan | 264/9 |

OTHER PUBLICATIONS

Fujita et al. J.O.C. vol. 44 (No. 15), 1979, pp. 2647–2651.

Primary Examiner—Alan Siegel
Assistant Examiner—John Peabody
Attorney, Agent, or Firm—JoAnn Villamizar

[57] ABSTRACT

The present invention relates to a process for the manufacture of granules of low-melting alkyl ester containing hindered hydroxylphenyl groups, which comprises
(a) extracting a melt of crude alkyl ester containing hindered hydroxylphenyl groups with an aqueous alcoholic solution of N,N-dibenzylhydroxylamine (DBHA),
(b) granulating the extracted melt by introducing said melt into an aqueous alcoholic solution maintained under a turbulent state at a temperature below 20° C., and
(c) isolating the resulting granules.

23 Claims, No Drawings

EXTRACTIVE PURIFICATION OF PHENOLS

BACKGROUND OF THE INVENTION

Alkylated phenols, such as those which are sterically hindered, are widely used as stabilizers, as they inhibit, for example, oxidative and thermal degradation of a wide range of polymeric systems. These stabilizers are, for example, employed in an amount of about 0.01 to about 5% by weight, preferably about 0.01 to about 0.05% by weight, based upon the stabilized mixture. The levels of stabilizers in the polymer may vary considerably depending on the particular end use application, the degree of protection against degradation, variations in substrate, and the presence of synergizing stabilizers such as thermal stabilizers or ultraviolet light absorbers, and dyes or pigments. The stabilized polymer compositions are prepared by a number of means, for example, by mixing into thermoplastic substrates, or by dissolving in a co-solvent and mixing into a substrate solution. Many process variants for the manufacture of corresponding phenols having antioxidative properties have been developed. However, impurities, such as quinones, adversely effect the stability and, hence, the quality of the alkylated phenols. Accordingly, there are intensive efforts in the art to develop purification processes to avoid these disadvantages.

U.S. Pat. No. 4,386,224 relates to a method for stabilizing color and for reducing color of monoalkyl phenol compositions by addition of N,N-diethylhydroxylamine.

U.S. Pat. No. 3,285,855 describes the manufacture of alkylated phenols containing an alkyl ester group which can be used for the stabilization of synthetic organic polymers against oxidative degradation.

U.S. Pat. No. 4,316,996 discloses a process for the manufacture of phenolic antioxidants as well as a method of purifying the resulting phenols. The purification step first provides the neutralization of the used catalyst by addition of an aqueous base (e.g. $Na_2CO_3$) and an alkyl substituted hydroxylamine and then, in a next step, the addition of an oxime and an alkyl substituted hydroxylamine. No granulation process is disclosed.

There is a strong ned for using granules of antioxidative alkylated phenols in the manufacture of polymers, such as polybutadienes, polyvinylchlorides and polystyrenes, since crystallized products are not sufficiently suitable for the corresponding application of the phenols. Furthermore, the handling of the granules is more convenient in the application process of the phenols. U.S. Pat. No. 5,006,284 discloses the manufacture of granules of sterically hindered phenols having antioxidative activities by introducing the melt of the manufactured phenols into an aqueous solution of methanol and isolating the granules. However, if such granules are partially obtained in the form of dust, this may impose difficulties in packing, transportation and handling in the industrial process. Accordingly, there is still a desire to optimize the properties of the resulting granules, for example, in terms of further reducing the amount of dust in the granules and especially in the enhancement of the long term color stability of the alkylated phenols.

SUMMARY OF THE INVENTION

The present invention relates to a process for the manufacture of granules of low-melting alkyl ester containing hindered hydroxylphenyl groups, which comprises (a) extracting a melt of crude alkyl ester containing hindered hydroxylphenyl groups with an aqueous alcoholic solution of N,N-dibenzylhydroxylamine (DBHA), (b) granulating the extracted melt by introducing said melt into an aqueous alcoholic solution maintained under a turbulent state at a temperature below 20° C., and (c) isolating the resulting granules. The resulting alkyl ester containing hindered hydroxylphenyl groups exhibit excellent antioxidant properties and significantly improved long term color stability.

DETAILED DESCRIPTION OF THE INVENTION

Surprisingly, when using the process according to the present invention, uniform, free-flowing and substantially dust-free granules are obtained which significantly reduce or substantially eliminate quinone by-products and improve the long term color stability of the alkyl ester containing hindered hydroxylphenyl groups and hence the quality of the such treated esters.

The present invention relates to a process for the manufacture of granules of low-melting alkyl ester containing hindered hydroxylphenyl groups, which comprises (a) extracting a melt of crude alkyl ester containing hindered hydroxylphenyl groups with an aqueous alcoholic solution of N,N-dibenzylhydroxylamine (DBHA), (b) granulating the extracted melt by introducing said melt into an aqueous alcoholic solution maintained under a turbulent state at a temperature below 20° C., and (c) isolating the resulting granules.

Alkyl esters containing hindered hydroxylphenyl groups are, for example, compounds of the formula

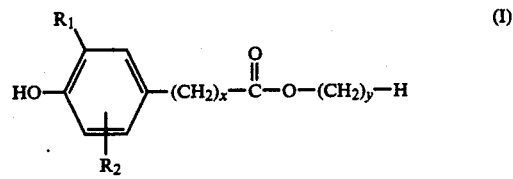

wherein
$R_1$ and $R_2$, independently of each other, are $C_1$–$C_8$-alkyl;
x is an integer from 0 to 6; and
y is an integer from 1 to 30.

$C_1$–$C_8$-Alkyl is, for example, methyl, ethyl, n-propyl, isopropyl, n-butyl, sec-butyl, tert-butyl, or tert-pentyl. Preferred is $C_1$–$C_5$-alkyl, especially corresponding branched lower alkyl groups, for example, isopropyl, tert-butyl and tert-pentyl.

Preferred are those compounds of the formula I, wherein $R_1$ is located in ortho position or especially wherein $R_1$ and $R_2$ are located in meta or especially in ortho position, relative to the phenolic hydroxyl group.

Preferred compounds of the formula I are those wherein $R_1$ and $R_2$, independently of each other, are isopropyl, tert-butyl or tert-pentyl, or one of the substituents is methyl and the other is isopropyl, tert-butyl or tert-pentyl.

Especially preferred are compounds of the formula I, wherein x is an integer from 1 to 3, in particular 2, and y is an integer from 6 to 20, preferably an integer from 12 to 20, for example 16 or 18.

An especially preferred phenol is methyl or, in particular, octadecyl 3-[(3,5-di-tert-butyl-4-hydroxy)-phenyl]propionate.

A low-melting alkyl ester containing hindered hydroxylphenyl groups has, for example, a melting point anywhere between about 20° C. to about 100° C. Preferably, the melting point is in the range of 30° C. to 80° C., for example, about 50° C. It is understood that the process of the present invention applies also to the alkyl esters having a melting point above 100° C. when in a pure state, but which contain manufacturing by-products or impurities which lower the melting point. Such impurities are, for example, homologous alkyl esters wherein y is different from the value of y of the primary compound.

In the process of the invention, the temperature of the melt is preferably about 5° C. to about 30° C. above the melting point of the compound to be granulated, usually around 10° C. above the melting point so as to avoid unintentional crystallization and clogging in the melt.

The aqueous alcoholic solvent employed in the extraction step is a lower alcohol, e.g. $C_1$–$C_4$ alcohol, preferably methanol, ethanol or isopropanol, most preferably methanol. Generally, about 1 to 30 wt % water, preferably about 3 to 10 wt % water, most preferably, about 5 wt % water can be used.

Dialkyl or Diaralkylhydroxylamines [Tetrahedron Lett. 1695 (1975)] are mild and selective reducing agents of quinones. In the present invention, N,N-dibenzylhydroxylamine is used in an amount of about 0.5% to about 5% by weight, in relation to the alcoholic solvent. A preferred amount is about 0.75% to about 3% by weight, in relation to the alcoholic solvent.

The aqueous alcoholic solvent is employed in the extraction step in an amount of about 10–50 wt %, preferably about 20–40 wt %, and most preferably about 30 wt %, in relation to the crude alkyl ester.

In a preferred embodiment, a further extraction step is employed prior to granulation using an aqueous alcoholic solvent as defined above without the DBHA to remove any remaining impurities. The amount of solvent in relation to the alkyl ester is the same as in the extraction step with DBHA as set forth above.

The aqueous alcoholic solvent employed in the granulation step is a lower alcohol, e.g. $C_1$–$C_4$ alcohol, preferably methanol, ethanol or isopropanol. For example, for compounds to be granulated having a melting point below 60° C., methanol is the preferred lower alcohol, and for compounds having a melting point between 50° C. and 75° C., ethanol is the preferred lower alcohol. The ratio of water to lower alcohol is so chosen as to result in the desired granule particle size and size distribution and will depend upon the lower alcohol chosen and the compound to be granulated. In a preferred embodiment, wherein methanol is employed and contains between about 5 and 20 wt % water. As the water concentration decreases, the particle size decreases and the required time for granule formation increases. The particle size can therefore be determined by the amount of water used. A preferred amount of water is around 10 wt %, for example between 8 and 12 wt %.

The temperature of the agitated aqueous alcoholic solution is kept below room temperature, i.e. 20° C. The temperature is preferably kept between about 5° C. and 15° C. The solution is agitated in a manner causing turbulence. Any kind of equipment used for agitation is suitable, for example, conventional stirring at 50 revolutions per minute (rpm) or more, and preferably about 300 rpm.

The granule formation is preferably conducted under conditions wherein the melt is introduced in amounts less than about 5% by weight of the solvent, particularly about 2% or less.

Proper granulation occurs rapidly, for example, in about 0.5 minutes. More time may be required for granule curing when the ratio of water to alcohol is not at its optimum value or when the concentration of the melt introduced into the solution is above 2%. Nevertheless, proper granulation is still accomplished within reasonable periods of time, for example, within about 3 to about 5 minutes.

The solution containing the formed granules is then filtered, and the granules, if desired, sorted according to size. Granules have a spherical shape with smooth surface and flowing properties, are hard and are not allowed to substantially fragment into dust. A preferred size range of the granules is in the range of about 0.3 to about 2 mm, after wet granulation especially about 1000 μm to about 2000 μm. Oversize and undersize agglomerates may be returned to the melt.

The process of the invention may be conducted batchwise or in a continuous flow system. In a preferred embodiment of the invention, the melt of the compound to be granulated is added to the cold agitated aqueous alcoholic solution in a continuous flow system so as to keep the ratio of melt and solvent in the desired range.

In a further preferred embodiment, the present invention relates to a process for the purification of a melt of crude octadecyl 3-[(3,5-di-tert-butyl-4-hydroxy)-phenyl]propionate which comprises
  a) extracting the melt with an methanolic solution of N,N-dibenzylhydroxylamine;
  b) granulating the extracted melt by introducing said melt into an aqueous alcoholic solution maintained under a turbulent state at a temperature below 20° C.; and
  c) isolating the granules.

In the extraction step, the compound is melted at about 55° C. to about 65° C. and treated with about 0.1 to about 1.0% by weight of DBHA dissolved in 90–100% methanol in water. In the granulation step, the melt is added dropwise to a standard wet granulation apparatus into a cooled methanolic solution (about 85 to about 97%), the temperature preferably being about 5° C. to about 10° C. under moderate agitation.

The DBHA extraction/wet granulation process for antioxidant alkyl esters provides a product with increased color stability. The process also eliminates crystallization as the means to purify/isolate the alkyl esters which is currently the bottleneck of the industrial process. Wet granulation produces a dust-free, free-flowing granular alkyl ester antioxidant. The granules formed are of uniform size, hard with a smooth surface not susceptible to fragmentation.

The following table shows long term color stability by $PbO_2$ test and 7 Day Stability test.

| ANALYTICAL COMPARISON OF CRYSTALLIZED AND DBHA EXTRACTED IRGANOX 1076 | | | |
|---|---|---|---|
| Test | Spec. | DBHA 1076GR | Crystal |
| 425 nm TRANS | ≧95% | 98.8% | 97.6% |

-continued

ANALYTICAL COMPARISON OF CRYSTALLIZED AND DBHA EXTRACTED IRGANOX 1076

| Test | Spec. | DBHA 1076GR | Crystal |
|---|---|---|---|
| 500 nm TRANS | ≧97% | 99.4% | 99.2% |
| UV ASSAY | 98–102% | 98.9% | 98.6% |
| PbO2 (425 nm) | NO LIMIT | 99.0% | NT |
| 3 DAY (425 nm) | ≧95% | 98.7% | NT |
| 7 Day (425 nm) | ≧95% | 98.7% | 96.6% |

The following examples are intended to illustrate the invention and are not to be construed as being a limitation thereof. Percentages are given by weight.

EXAMPLE 1

Reaction Conditions for the N,N-dibenzylhydroxylamine (DBHA) Extraction of octadecyl 3-[(3,5-di-tert-butyl-4-hydroxy)-phenyl]propionate The title compound is prepared according to U.S. Pat. No. 3,285,855 and the crude phenolic reaction mass (500 grams) is melted at 60° C.–65° C. A solution of N,N-dibenzylhydroxylamine (DBHA) (0.1–1.0% weight to the reaction mass) is prepared by dissolving in 90–100% methanol in water (150 grams). The methanolic DBHA solution is added to the phenolic reaction mass at 60° C.–65° C. and held at that temperature with agitation for 2.5 hours. The agitation is stopped and the layers allowed to split (DBHA in methanol is the top layer and the phenolic reaction mass is the bottom layer). The DBHA layer in methanol is split from the phenolic reaction mass. The reaction mass is subsequently washed with 90–100% methanol and held at 60° C.–65° C. for 0.5 hours. Agitation is stopped and layers are allowed to split. The phenolic reaction mass is consequently wet granulated to form a desired final product.

EXAMPLE 2

Reaction Conditions for the N,N-dibenzylhydroxylamine (DBHA) Urea Extraction of octadecyl 3-[(3,5-di-tert-butyl-4-hydroxy)-phenyl]propionate The title compound is prepared according to U.S. Pat. No. 3,285,855 and the crude phenolic reaction mass (500 grams) is melted at 60° C.–65° C. A solution of N,N-dibenzylhydroxylamine (DBHA) (0.1–1.0% by weight to the reaction mass) and urea (0.1–1.0%) was prepared by dissolving in 90–100% methanol in water (150 grams). The methanolic DBHA/urea solution is added to the phenolic reaction mass at 60° C.–65° C. and held at that temperature, with agitation for 2.5 hours. The agitation is stopped and the layers allowed to split (DBHA/urea in methanol is the top layer and the phenolic reaction mass is the bottom layer). The DBHA/urea layer in methanol is split from the phenolic reaction mass. The reaction mass is subsequently washed with 90–100% methanol and held at 60° C.–65° C. for 0.5 hours. Agitation is stopped and layers area allowed to split. The phenolic reaction mass is consequently wet granulated to form a desired final product.

EXAMPLE 3

Reaction Conditions for the Granulation of octadecyl 3-[(3,5-di-tert-butyl-4-hydroxy)-phenyl]propionate The title compound is prepared according to U.S. Pat. No. 3,285,855 and is used as a wet cake containing 10% methanol. The compound is an off-white powder melting at 50° C.–55° C. The wet cake is melted at 60° C.–65° C. and added in a slow stream in a given concentration of between 0.59% and 2.65% to a continuous stream of aqueous methanol containing between 5% and 20% water kept at a temperature between 8° C. and 20° C. in two consecutive 2 liter round bottom jacketed reactors stirred at 300 rpm resulting in a turbulent state. The retention time in the reactors is calculated by the formula $$\frac{4000 \text{ ml}}{(\text{melt ml/min} + \text{solvent ml/min})}$$

and is between 0.52 and 2.25 min. Approximately 6 liter of solvent and 1 liter of melt are used for each test. The solids are sieved through a 50 mesh U.S. Standard Sieve and dried in a fluidized bed dryer. The undersized material is continuously recycled in the aqueous methanol. The dried solids are sieved through 10 mesh and 60 mesh sieves (U.S. Standard Sieve Series) and the relative amounts determined.

EXAMPLE 4

Continuous Flow Granulation of octadecyl 3-[(3,5-di-tert-butyl-4-hydroxy)-phenyl]propionate The title compound is prepared according to U.S. Pat. No. 3,285,855 and the crude phenolic reaction mass (500.0 grams) is melted at 60° C.–65° C. A solution of the reducing agents listed in the following table (0.4–2.0% by weight to the reaction mass) is prepared by dissolving in 90–100% methanol in water (150 grams). The methanolic solution of the reducing agent is added to the phenolic reaction mass at 60° C.–65° C. and held at that temperature, with agitation for 2.5 hours. The agitation is stopped and the layers allowed to split (reducing agent in methanol is the top layer and the phenolic reaction mass is the bottom layer). The reducing agent in methanol is split from the phenolic reaction mass. The reaction mass is subsequently washed with 90–100% methanol and held at 60° C.–65° C. for 0.5 hour. Agitation is stopped and the layers allowed to split. The phenolic reaction mass is consequently wet granulated to form a desired final product.

IRGANOX 1076 EXTRACTIVE PURIFICATION

| REDUCING AGENT | Analytical Test Results | | | |
|---|---|---|---|---|
| | CONC.* | 425 nm | 500 nm | PbO2 425 nm | 7-Day Stability 425 nm |
| N,N-dibenzylhydroxylamine (DBHA) | 0.75% | 98.8% | 99.4% | 99.0% | 98.7% |
| DBHA/Urea | 0.4%/0.4% | 99.3% | 99.7% | 98.7% | 98.9% |
| N,N-diethylhydroxylamine | 1.20% | 94.5% | 99.0% | 91.6% | — |
| N,N-dimethylhydroxylamine. HCl | 2.00% | 67.2% | 98.7% | 58.5% | — |

*Percent weight/weight based on Irganox 1076 Reaction Mass

The table compared various dialkylhydroxylamines as quinone reducing agents. The quinones once reduced are colorless and more soluble in the aqueous alcoholic solution. The resulting extracted phenolic layer is essentially colorless with increased long term color stability. The results establish that N,N-dibenzylhydroxylamine (DBHA) is superior to the comparative examples for maintaining color stability. The addition of urea as a complexing agent for the reduced form of the quinones allowed for further reduction in the reducing agent.

What is claimed is:

1. A process for the manufacture of granules of low-melting alkyl ester containing hindered hydroxylphenyl groups, which comprises
   (a) extracting a melt of crude alkyl ester containing hindered hydroxylphenyl groups of the formula:

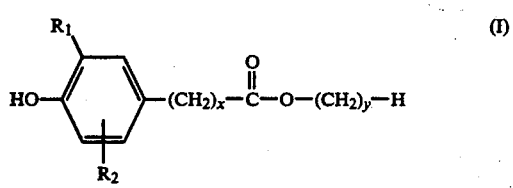

wherein
$R_1$ and $R_2$, independently of each other, are $C_1$–$C_8$-alkyl;
$x$ is an integer from 0 to 6; and
$y$ is an integer from 1 to 30 with an aqueous alcoholic solution of N,N-dibenzylhydroxylamine (DBHA),
   (b) granulating the extracted melt by introducing said melt into an aqueous alcoholic solution maintained under a turbulent state at a temperature below 20° C., and
   (c) isolating the resulting granules.

2. A process according to claim 1 wherein said aqueous alcoholic solution in step (a) is a lower alkanol.

3. A process according to claim 2 wherein said lower alkanol is methanol.

4. A process according to claim 1 wherein said N,N-dibenzylhydroxylamine is present in an amount of about 0.5% to about 5% by weight, in relation to the alcoholic solvent.

5. A process according to claim 1 wherein said N,N-dibenzylhydroxylamine is present in an amount of about 1.5% to about 3% by weight, in relation to the alcoholic solvent.

6. A process according to claim 1 wherein said aqueous alcoholic solution contains about 1 to about 30 wt % water.

7. A process according to claim 1 wherein said aqueous alcoholic solution contains about 3 to about 10 wt % water.

8. A process according to claim 1 wherein said aqueous alcoholic solution contains about 5 wt % water.

9. A process according to claim 1 wherein $R_2$ is in an ortho position to the hydroxy function, $x$ is 1, 2 or 3 and $y$ is an integer from 6 to 30.

10. A process according to claim 1 wherein the melting point of the alkyl ester containing hindered hydroxyphenyl groups is between 20° C. and 100° C.

11. A process according to claim 10 wherein the melting point is between 30° C. and 80° C.

12. A process according to claim 1 wherein said aqueous alcoholic solution in step (b) is a lower alkanol.

13. A process according to claim 12 wherein said lower alkanol is methanol.

14. A process according to claim 1 wherein the temperature of the aqueous alcoholic solution in step (b) is between 5° C. and 15° C.

15. A process according to claim 1 wherein the alkyl ester is octadecyl 3-[(3,5-di-tert-butyl-4-hydroxy)-phenyl]propionate and wherein the aqueous alcoholic solution in step (b) is maintained at a temperature below 15° C.

16. A process according to claim 15 wherein the temperature of the melt is between 55° C. and 80° C.

17. A process according to claim 15 wherein the melt contains between 5–15% methanol.

18. A process according to claim 1 wherein the aqueous alcoholic solution in step (b) contains between 5 and 20 wt % water.

19. A process according to claim 1 wherein the aqueous alcoholic solution in step (b) contains between 8 and 12 wt % water.

20. A process according to claim 1 wherein the melt introduced into the aqueous alcoholic solution does not exceed 5%.

21. A process according to claim 1 wherein the melt introduced into the aqueous alcoholic solution does not exceed 2%.

22. A process according to claim 1 wherein the said aqueous alcoholic solution in step (a) is employed in an amount of about 10 to 50 wt % in relation to the crude alkyl ester.

23. A process according to claim 1 wherein the said aqueous alcoholic solution in step (a) is employed in an amount of about 30 wt % in relation to the crude alkyl ester.

* * * * *